United States Patent [19]

Hegde et al.

[11] Patent Number: 5,026,731
[45] Date of Patent: Jun. 25, 1991

[54] PHARMACEUTICAL COMPOSITION AND METHOD OF TREATING PSYCHOSES

[75] Inventors: Vinod R. Hegde, Rockaway; Mahesh G. Patel, Verona, both of N.J.

[73] Assignee: Schering Corporation, Kenilworth, N.J.

[21] Appl. No.: 537,178

[22] Filed: Jun. 13, 1990

[51] Int. Cl.$^5$ .............................................. A61K 3/16
[52] U.S. Cl. ................................................ 514/629
[58] Field of Search ........................................ 514/629

[56] References Cited

PUBLICATIONS

A. J. Streeter et al., Drug metabolism and Disposition, vol. 12, 565–576.
A. J. Streeter, et al., Biochemical Pharmacology (1985) vol. 34, 2871–2876.

*Primary Examiner*—Stanley J. Friedman
*Attorney, Agent, or Firm*—Thomas D. Hoffman; Gerald S. Rosen

[57] ABSTRACT

A method of treating psychoses in a mammal which comprising administering to a mammal in need of such treating an antipsychotic effective amount of a compound represented by

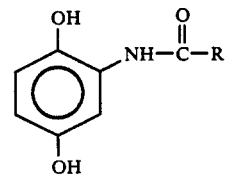

wherein R is a ($C_1$–$C_9$) straight or branched chain alkyl group or a pharmaceutical composition thereof is disclosed.

5 Claims, No Drawings

PHARMACEUTICAL COMPOSITION AND METHOD OF TREATING PSYCHOSES

BACKGROUND

This invention relates to a method of treating psychoses in mammals by administering to mammals in need to such treating an antipsychotic effective amount of 2,5-dihydroxy ($C_2$–$C_{10}$) alkanoylanilide, e.g. 2-, 5-dihydroxyacetanilide or a pharmaceutical compositions thereof.

Acetanilide, 3-hydroxyacetanilide and 4-hydroxyacetanilide (acetamnophen) are known analgesic and anti-pyretic agents. A. J. Streeter et al. in *Drug Metabolism and Disposition* (1984) Vol. 12, p 556-567 disclose that 2-,5-dihydroxyacetanilide has been isolated as the primary metabolite of 3-hydroxyacetanilide. See also A. J. Streeter et al. *Biochemical Pharmacology* (1985) Vol. 34, p 2871-2876 which discloses 2,5-dihydroxyacetanilide binds inreversibly to microsomal protein. There is no disclosure, however, of the present invention.

THE SUMMARY OF THE INVENTION

The present invention provides a pharmaceutical composition for treating pyschoses in a mammal which comprises an antipsychotic effective amount of a compound represented by

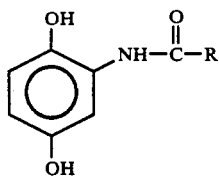

wherein R is a $C_1$ to $C_9$ straight or branched chain alkyl group;
and a pharmaceutical acceptable carrier therefor.

The present invention also provides a method of treating psychoses in a mammal which comprises administering to a mammal in need of such treating an anti-psychotic effective amount of a compound represented by formula I
or a pharmaceutical composition thereof.

DESCRIPTION OF THE INVENTION AND OF THE PREFERRED EMBODIMENTS

Typical suitable $C_1$–$C_9$ straight and branched alkyl groups include methyl, ethyl, n-and iso-propyl, n-, iso, sec and tert-butyl, n-, iso sec-tert-and neo-pentyl, n-, iso, sec, tert-hexyl, n, iso, sec, tert-heptyl, n-, iso, sec, tert-octyl and n, iso, sec-tert-norajl. The preferred alkyl group is methyl.

Compounds represented by formula I are prepared from 2,5-dimethoxyaniline (available from Aldrich Chemical Co, Milwaukee, WI). by N-acylation (e.g. via by use of an hydrides or alkanoyl halides) followed by O-dimethylation with iodotrimethylsilane in accordance with the procedure for the preparation of the preferred compound of this invention, i.e. 2,5-dihydroxyacetanilide reported by A. J. Streeter et al. in *Drug Metabolism & Disposition*. (1984) Vol 12, pp 565-576 at page 568.

The compounds represented by formula I display antipsychotic activity in the following test procedure.

COMPETITIVE INHIBITION ASSAY

Many compounds capable of effecting reproducible physiological changes in nervous system tissues are believed to operate by binding at one or more receptor sites. Compounds which interact strongly with these receptor sites in on in vitro test, using homogenates of the target organ or structure, are expected to exhibit similar properties when administered in vivo and are, therefore, candidates for continued study as potential therapeutic and/or diagnostic agents.

Binding of a compound to a receptor sites, in vitro, is demonstrated by the specificity of binding and the saturability of the available sites. A modification of the methodology for characterization of D-1 and D-2 receptor binding and an interpretation of the data as described by Billard et al., *Life Sciences* 35, 1885 (1984) was used in which the binding of the benzazepine (R)-(+)-8-chloro-2,3,4,5-tetrahydro-3-methyl-5-phenyl-1H-3-benzazepin-7-ol hemimaleate (Sch 23390) to the dopamine D-1 receptor binding as compared to D-2 receptor binding is believed to confer the therapeutic advantage of avoiding troublesome and potentially irreversible neurological side effects associated with D-2 receptor occupancy.

MATERIALS AND METHODS

Tritiated Sch 23390 and tritiated spiperone (a potent D-2 receptor ligand) were obtained as described in the Billard et al. reference supra and serially diluted in 0.05M Tris buffer, pH 7.4, as required. Compounds of represented by formula I may be synthesized as disclosed herein and diluted in 0.05M Tris buffer, pH 7.4, as required.

TISSUE PREPARATION

Bovine brains were obtained from a local slaughter house, on ice. Striata were dissected on ice and membranes prepared as described earlier (Billard et al., supra, 1984) for rat brain. Briefly, the striata were homogenized in 20 volumes of Tris-HCl (50 mM) buffer, pH 7.4, using a Polytron (Brinkmann) homogenizer, setting 7; membranes were washed by centrigugation (20,000×g) and resuspending in buffer, twice, and finally resuspended in assay buffer (Tris-HCl, 50 mM, pH 7.4, containing 120 mM NaCl, 5 mM KCl, 2 nM $CaCl_2$, 1 mM $MgCl_2$). At least 3-4 different pools of membrane were processed and stored at −80° C.

ASSAY

Binding analysis of $^3$H-Sch 23390 ($D_1$-binding) (Amersham, MN) and $^3$H-spiperone ($D_2$-binding) (NEN, MA) were performed in triplicate using a final incubation volume of 500 μl with Tris-HCl buffer (50 mM, pH 7.4, containing 120 mM NaCl, 5 mM HCl, 2 nM $CaCl_2$, 1 mM $MgCl_2$) and containing 2 mg of tissue per tube. Non-specific binding was defined with 1 μM of Sch 23390 for $D_1$-binding and 1 μM of (+) butaclamol for $D_2$-binding, respectively. For competition studies, several concentration of test drug or standard were included, ranging from $10^{-4}$ to $10^{-3}$. Tubes were incubated, 30 minute incubations at 37° C. were terminated by rapid filtration under vacuum, on to GF/B filters, presoaked in 0.3% polyethyleneamine (PEl), with three 5 ml washes. Kinetic analyses for the inhibition constant (Ki) were performed using the LUNDON 2 computer program for competition analysis (LUNDON Software Inc., Ohio) based on methods disclosed by Cheng, Y. C. and Pruschoff, W. H. "Relationship Between the Inhibition Constant (Ki) and the Concentration of Inhibitor That Causes 50 Percent Inhibition (I50) of an Enzymatic Reaction", *Bio. Chem. Pharmacol.*, (1973) 22: 3099–3108 and Feldman, H. A. "Mathematical Theory of Complex Ligand-Binding Systems at Equilibrium: Some Methods of Parameter Fitting", *Anal. Biochem.*, (1972) 48: 317–338. Protein was measured by the method disclosed by Lowry, O.H., Rosebrough, N.J., Farr, A.L. and Randall, R.J. "Protein Measurement with Folin-Phenol Reagent", *J. Biol. Chem.*, (1951) 193:265–275.

TABLE 1

| Kinetic Analysis for 2,5-Dihydroxyacetanilide | | |
|---|---|---|
| Drug | D1 | D2 |
| | $K_i(\mu M)$ | |
| Sch 23390 | 0.0008 | 0.8 |
| (+) butaclamol | 0.015 | 0.001 |
| 2,5-dihydroxyacetanilide | 1.2–2 | 200 |

The data listed in Table 1 demonstrate that 2-5-dihydroxyacetanilide is a more than 100 fold selective D1 receptor.

The comparatively small $K_i$ values of 2-,5-dihydroxyacetanilide in the competitive binding assay with Sch 23390 indicate that the compounds represented by formula I would bind strongly to the D-1 receptor site. The relatively high $K_i$ values for the D-2 site, for which spiperone is highly selective, indicate that the compounds represented by formula I would not specifically be bound to that receptor site.

For preparing pharmaceutical compositions from the compounds of formula I, inert, pharmaceutically acceptable carriers are admixed with the active compounds. The pharmaceutically acceptable carriers may be either sold or liquid. Solid form preparations include powders, tablets, dispersible granules, capsules, cashets and suppositories. A solid carrier can be one or more substances which may also act as diluents, flavoring agents, solubilizers, lubricants, suspending agents, binders or tablet disintegrating agents; it may also be an encapsulating material. In powders, the carrier is a finely divided solid which is in admixture with the finely divided active compound. In the tablet, the active compound is mixed with a carrier having the necessary binding properties in suitable proportions and compacted in the shape and size desired. The powders and tablets typically contain from 5 to about 70% of the active ingredient dependent upon the potency of the active compound, the size and age of the intended user, and the range of dosage required for the specific therapy. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter and other materials typically "preparation" is intended to include the formulation of the active compound with encapsulating material as carrier, providing a capsule in which the active component (with or without other carriers) is surrounded by a carrier, which is thus in association with it. Similarly, cachets are included. Tablets, powders, cachets and capsules can be used as solid dosage forms suitable for oral administration.

For preparing suppositories, a low melting wax such as a mixture of fatty acid glycerides or cocoa butter is first melted and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or waterpropylene glycol solutions for parenteral injection. Liquid preparations can also be formulated in solution in aqueous polyethylene glycol solution. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Also including are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. The solid form preparations intended to be converted to liquid form may contain, in addition to the active material, flavorants, colorants, stabilizers, buffers, artificial and natural teaspoon or other volumetric container. The solid form preparations intended to be converted to liquid form may contain, in addition to the active material, flavorants, colorants, stabilizers, buffers, artificial and natural sweetners, dispersants, thickeners, zing solubilizing agents and the like. The solvent utilized for preparing the liquid form preparation may be water, isotonic aqueous salt solutions, ethanol, glycerine, propylene glycol and the like, as well as mixtures thereof. The solvent utilized will be chosen with regard to the route of administration. For example, liquid preparations containing large amounts of ethanol are not generally suitable for parenteral use.

The invention also contemplates alternative delivery systems including, but not necessarily limited to, transdermal delivery. The transdermal compositions can take the form of creams, lotions and/or emulsions and can be included in a transdermal patch of the matrix or reservoir type as are conventional in the art of this purpose.

Preferably, the pharmaceutical preparation is in unit dosage form. In such form, the preparation is subdivided into unit doses containing appropriate quantities of the active components. The unit dosage form can be a packaged preparation, the package containing discrete quantities of preparation such as packeted tablets, capsules and powders in vials or ampules. The unit dosage form can also be a capsule, cachet or tablet itself, or it may be the appropriate number of any of these in a packaged form.

The quantity of active compound in a unit dose preparation may be varied or adjusted from 1 mg to 100 mg according to the particular application and the potency of the active ingredient and the intended treatment. This would correspond to a dose of about 0.02 to about 2.0 mg/kg which may be divided over 1 to 3 administrations per day. The composition may, if desired, also contain other therapeutic agents.

The dosages may be varied depending on the requirement of the patient, the severity of the condition being treating and the particular compound being employed. Determination of the proper dosage for a particular situation is within the skill of those in the medical art. For convenience, the total daily dosage may be divided and administered in portions throughout the day or by means providing continuous delivery.

EXAMPLE #1

Preparation of 2-5-Dihydroxy ($C_3$–$C_{10}$) Alkanoylanilides

The procedure of Streeter et al supra at p565 and 567 for the preparation of 2,5-dihydroxyacetanilide is used except that a stoichiometric equivalent amount of the appropriate ($C_3$–$C_{10}$) alkanoyl chloride is substituted for acetyl chloride to provide the corresponding 2,5-dimethoxy ($C_3$–$C_{10}$) alkanoylanilide. The demethylation procedure with iodotimethylsilane is followed to provide the corresponding 2-,5-dihydroxy ($C_3$–$C_{10}$)alkanoylanilide.

What is claimed is:

1. A method of treating psychoses in a mammal which comprises administering to a mammal in need of such treating an antipsychotic effective amount of a compound represented by

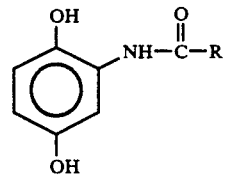

wherein R is a $C_1$ to $C_9$ straight or branched chain alkyl group or a pharmaceutical composition thereof.

2. A method of claim 1 wherein R is $CH_3$.
3. A method of claim 1 wherein the administering is done orally.
4. A method of claim 1 wherein the administering is done parenterally.
5. A method of claim 1 wherein the administering is done systemically.

* * * * *